United States Patent
Merchant

(10) Patent No.: US 8,341,850 B2
(45) Date of Patent: Jan. 1, 2013

(54) APPARATUS FOR MEASURING ANATOMIC ANGLES

(76) Inventor: Alan Craig Merchant, Los Altos, CA (US)

( * ) Notice: Subject to any disclaimer, the term of this patent is extended or adjusted under 35 U.S.C. 154(b) by 38 days.

(21) Appl. No.: 12/807,841

(22) Filed: Sep. 15, 2010

(65) Prior Publication Data

US 2011/0071437 A1    Mar. 24, 2011

Related U.S. Application Data

(60) Provisional application No. 61/276,909, filed on Sep. 18, 2009.

(51) Int. Cl.
*G01B 3/56* (2006.01)
*A61B 5/103* (2006.01)

(52) U.S. Cl. ............... 33/471; 33/512; 33/1 N

(58) Field of Classification Search ............ 33/1 N, 33/418, 419, 421, 424, 425, 426, 465, 471, 33/472, 473, 512, 456, 457, 458, 459, 478, 33/495, 496, 497, 498, 499, 500; 600/587, 600/595; D10/65
See application file for complete search history.

(56) References Cited

U.S. PATENT DOCUMENTS

| | | | | | |
|---|---|---|---|---|---|
| 330,837 | A | * | 11/1885 | Judd | 33/458 |
| 475,390 | A | * | 5/1892 | Downey | 33/500 |
| 803,349 | A | * | 10/1905 | Liner | 33/458 |
| 1,184,579 | A | * | 5/1916 | Sefton | 33/457 |
| 1,299,978 | A | * | 4/1919 | MacDowney | 33/471 |
| 1,501,588 | A | * | 7/1924 | Ellison | 33/456 |
| 1,585,563 | A | * | 5/1926 | Schlattau | 33/471 |
| 1,979,567 | A | * | 11/1934 | Nicholson | 33/458 |
| 2,529,640 | A | * | 11/1950 | Thomas | 33/471 |
| D204,805 | S | * | 5/1966 | Gartman et al. | D10/65 |
| 3,269,015 | A | * | 8/1966 | Barker | 33/27.08 |
| 3,270,420 | A | * | 9/1966 | Simril | 33/471 |
| 3,431,653 | A | * | 3/1969 | Mudon | 33/458 |

(Continued)

FOREIGN PATENT DOCUMENTS

CH        674454 A5 *    6/1990

(Continued)

OTHER PUBLICATIONS

Lafayette Gollehon Extendable Goniometer, from the Human Evaluation, Range of Motion website for Lafayette Instrument Company, 2 pages as printed on Oct. 25, 2012, Known to Applicant on or before Sep. 15, 2010.*

*Primary Examiner* — R. A. Smith
(74) *Attorney, Agent, or Firm* — Pandiscio & Pandiscio

(57) ABSTRACT

A device for measuring anatomic angles with two arms and a fastener for securing them together at one end providing a pivot. One arm has degree markings around the pivot and the other has a marker to indicate the angle between the two. One or both arms have a method for extending and contracting their length. The device is sufficiently small and light to allow ease of portability in a clothing pocket. In a preferred embodiment the arms are made of thin, clear, light plastic to allow ease of portability as well as inexpensive manufacture. In another preferred embodiment the arms are made of metal, or other heat-resistant material, to allow autoclave sterilization for use during surgery. In a further preferred embodiment the method to allow extension and contraction of one or both arms is by affixing thin, tubular, telescoping metal sleeves to one or both arms.

10 Claims, 2 Drawing Sheets

U.S. PATENT DOCUMENTS

| | | | | |
|---|---|---|---|---|
| 4,223,445 A * | 9/1980 | Goodland | | 33/194 |
| 4,442,606 A * | 4/1984 | Graham et al. | | 33/1 N |
| 4,562,649 A * | 1/1986 | Ciavarella | | 33/419 |
| 4,813,149 A * | 3/1989 | Herkimer | | 33/462 |
| 4,866,853 A * | 9/1989 | Braden | | 33/465 |
| D337,955 S * | 8/1993 | Edwards | | D10/65 |
| 5,678,317 A * | 10/1997 | Stefanakos | | 33/512 |
| 6,470,586 B2 * | 10/2002 | Kneipp | | 33/529 |
| 6,804,895 B2 * | 10/2004 | Shapiro | | 33/471 |
| 6,823,603 B1 * | 11/2004 | Tindall | | 33/471 |
| 6,978,550 B2 * | 12/2005 | Xieh | | 33/27.02 |
| 7,293,363 B1 * | 11/2007 | Parker | | 33/471 |
| 7,571,548 B2 * | 8/2009 | Taylor et al. | | 33/512 |
| 7,614,155 B2 * | 11/2009 | Healey | | 33/195 |
| 2003/0226268 A1 * | 12/2003 | Gibson | | 33/281 |
| 2004/0107592 A1 * | 6/2004 | Matlis | | 33/512 |
| 2007/0276296 A1 * | 11/2007 | Bright et al. | | 600/595 |
| 2010/0205817 A1 * | 8/2010 | Nunes et al. | | 33/512 |
| 2012/0253235 A1 * | 10/2012 | Pellis | | 600/595 |

FOREIGN PATENT DOCUMENTS

| | | | |
|---|---|---|---|
| CN | 201248708 Y | * | 6/2009 |
| CN | 201637361 U | * | 11/2010 |
| CN | 202345161 U | * | 7/2012 |
| DE | 10014397 A1 | * | 10/2001 |
| ES | 2080682 A2 | * | 2/1996 |
| JP | 2012098127 A | * | 5/2012 |
| WO | WO 9407108 A1 | * | 3/1994 |

* cited by examiner

APPARATUS FOR MEASURING ANATOMIC ANGLES

CROSS REFERENCE TO RELATED APPLICATIONS

This application is based on provisional application Ser. No. U.S. 61/276,909, filed on Sep. 18, 2009.

STATEMENT REGARDING FEDERALLY SPONSORED RESEARCH OR DEVELOPMENT

Not Applicable

DESCRIPTION OF ATTACHED APPENDIX

Not Applicable

BACKGROUND OF THE INVENTION

This invention relates generally to the field of medical diagnosis and more specifically to an apparatus for measuring anatomic angles. There are many health professionals involved in the care and treatment of patients with musculoskeletal injuries and diseases. These include Orthopedic Surgeons, Physiatrists, Rheumatologists, Physical Therapists, Physical Therapy Assistants, Physician's Assistants, Athletic Trainers, Personal Trainers, etc. Almost all of these health Professionals use goniometers. A goniometer, or protractor, is an instrument to measure angles. Specifically, when used for musculoskeletal problems, the goniometer has two arms extending from a pivot point. Angular degrees are marked around this pivot, or center of rotation. These musculoskeletal specialists use goniometers to measure joint angles, ranges of joint motion, and other angular measurements, such as angles of limb alignment ("bow legs" and "knock knees"), and the quadriceps angle (Q angle). The anatomic Q angle is the complementary angle of the angle measured from the Anterior Superior Iliac Spine (ASIS) at the front of the pelvis to the center of the Patella (kneecap) to the Tibial Tubercle (the bump on the front of the knee below the kneecap).

These health professionals commonly use an inexpensive short (7-8 inch), light, plastic goniometer, which is very handy and convenient to carry in a pocket. However, its small arms fail to provide accurate measurements for the large joints (shoulder, elbow, wrist, hip, knee, and ankle) where the bony landmarks can be 18 inches from the apex. Furthermore, when it is used as a protractor to measure the Q angle, the long distance between the ASIS (the prominent bone on each side of the front of the pelvis) and the patella or kneecap, which can be as much as 24 inches away, makes accuracy impossible.

Physical Therapists and their assistants, who frequently require accurate, serial angular joint measurements, solve this problem by using the somewhat more accurate, larger, but more awkward, long-armed 14-inch goniometers. These are most frequently made of metal or plastic. Physicians and others, who do not require very accurate measurement of joint angles, almost always rely solely on the small pocket goniometers. However, accurate measurements are required for the care and treatment of angular knee deformities: genu varum (bow legs) and genu valgum (knock knees). For more accurate measurement of these deformities orthopedic surgeons have turned to plain x-rays. However, this small goniometer supplies inaccurate estimates for the Q angle. Studies have proven that Physicians and Surgeons need accurate measurements of the Q angle for proper diagnosis and treatment of the most frequent knee complaint: anterior knee pain and related conditions such as patellar dislocations. About 15 years ago, because Q angle measurements were so inaccurate, and because plain x-rays cannot be used to measure the Q angle, many studies began to advocate using a measuring technique based on a Magnetic Resonance Image (MRI). This certainly improves the accuracy, but at a huge increase in cost. One MRI of the knee can cost between $3936 and $1044, at least in Northern California.

Many years ago the Lafayette Instrument Company produced a goniometer with extendable and contractible arms, but for a variety of reasons it did not prove to be popular or useful.

For many decades, the most popular and common instrument to be used for measurement of anatomic angles has been the small (approximately 8"×2"×0.125"), inexpensive, plastic, pocket goniometers/protractor. For those health professionals who desire greater accuracy, plastic goniometers are available in various sizes up to those with arms of 14 inches in length. Goniometers of similar and varied sizes are also available made of metal, which can be sterilized with high-pressure steam for use during surgery. One goniometer/protractor for measuring anatomic angles, which has extendable and retractable arms, has been manufactured by Lafayette Instrument Company, Inc.; however, this goniometer cannot be steam-sterilized for use in the operating room during surgery.

All of these prior goniometers have deficiencies that limit their usefulness. The most popular, small, inexpensive, pocket goniometer lacks accuracy for measuring anatomic angles when the anatomic landmark or landmarks are at a distance greater than 8 inches from the apex or pivot point of the goniometer; the greater the distance, the greater the error.

The large 14-inch goniometers are bulky, awkward, and not easily portable. They also lose accuracy when the anatomic landmark or landmarks are at a distance of greater than 14 inches from the apex or pivot point of the goniometer; again, the greater the distance, the greater the error.

The goniometer/protractor with extendable and retractable arms manufactured by Lafayette Instrument Co., Inc. has several deficiencies. It's length of 8 inches improves its portability, however its width of 2½ inches and thickness of more than 2¾ of an inch makes it too bulky to carry in a pocket easily. Its weight of 4 ounces is more than four times heavier than the popular small pocket goniometers, again decreasing portability. It uses a small magnifying glass mounted on one arm to read the degree marks mounted on the other, however this small magnifying window does not let in sufficient light to allow easy observation in a lowlight environment. Finally, its cost to manufacture is so high that it is approximately 20 times more expensive than the common small pocket goniometers. These deficiencies apparently account for the fact that it is rarely used in clinical practice.

BRIEF SUMMARY OF THE INVENTION

The primary advantage of the invention is to improve the state of the prior art in contributing an instrument to make angular anatomic measurements having a degree of portability, practicality, affordability, and flexibility heretofore unknown.

Another advantage of the invention is to provide a measuring instrument that is less expensive to manufacture yet equally accurate and reliable.

Another advantage of the invention is to provide a measuring instrument that is lighter and smaller and thus more portable and useful.

Another advantage of the invention is to provide a measuring instrument that is fashioned of metal, or other heat resistant material, so that it can be sterilized in an autoclave for use during a surgical operation.

A further advantage of the invention is to provide a means of measuring anatomic angles that have both short and long distances between anatomic landmarks and the apex or pivot point of the angle to be so measured with equal accuracy and efficiency.

Other objects and advantages of the present invention will become apparent from the following descriptions, taken in connection with the accompanying drawings, wherein, by way of illustration and example, an embodiment of the present invention is disclosed.

In accordance with a preferred embodiment of the invention, there is disclosed a device for measuring anatomic angles, said device comprising: two pieces or arms with a means for securing one to the other at one end providing a pivot point, having degree markings around the pivot point on one arm and a marker or markers on the other arm to indicate the angle between the two arms, with a method or means on one or both arms for extending the length of said arm or arms with the ability of said method or means to retract or shorten said arm or arms to the original size, said device being sufficiently small and light to allow ease of portability in a clothing pocket.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

DETAILED DESCRIPTION OF THE PREFERRED EMBODIMENTS

Figure 1:
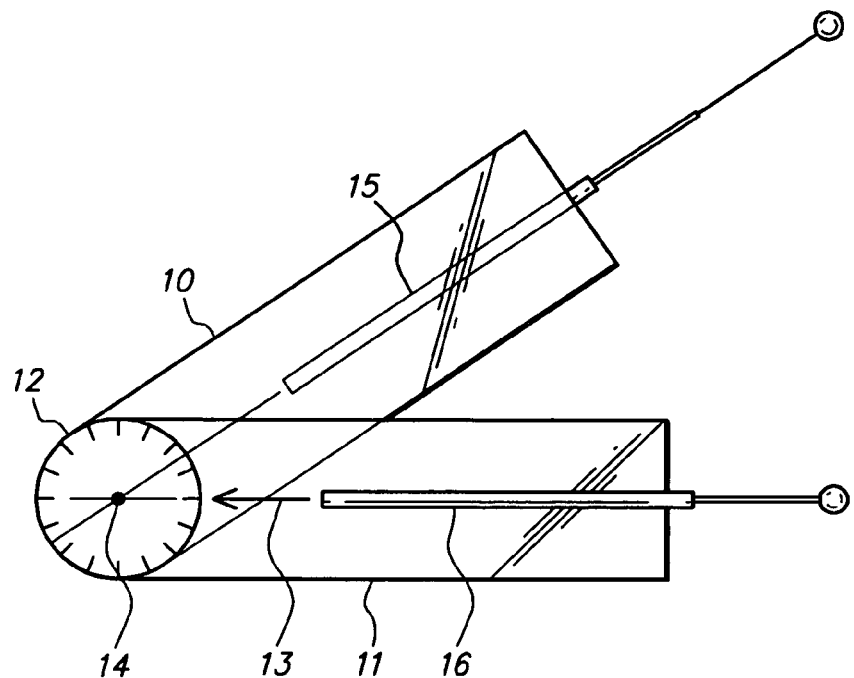
FIG. 1. is a plan view of the invention.
Figure 2:
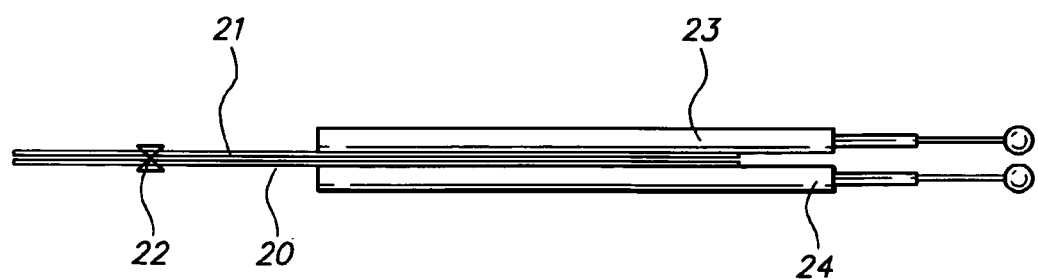
FIG. 2. is a side view of the invention.
Figure 3:
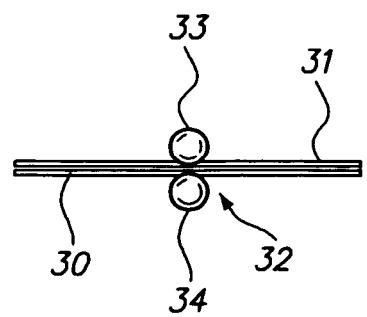
FIG. 3. is an end view of the invention.

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner. Turning now to the drawings, FIG. 1 is a Plan View of the device comprising arm 10 with degree markings 12, arm 11 with indicator marks or marks 13, and a fastener 14 creating a pivot at one end. FIG. 2 is a Side View of the device comprising arm 20 with degree markings, arm 21 with indicator mark or marks, and fastener 22 at one and creating a pivot point. FIG. 3 is an End View of the device comprising arm 30 with degree markings, arm 31 with indicator mark or marks, and fastener 32 at one and creating a pivot point.

The preferred embodiment illustrated in FIGS. 1-3 shows that the two arms are made of light, clear plastic for reduced expense and ease of portability.

Figure 4:
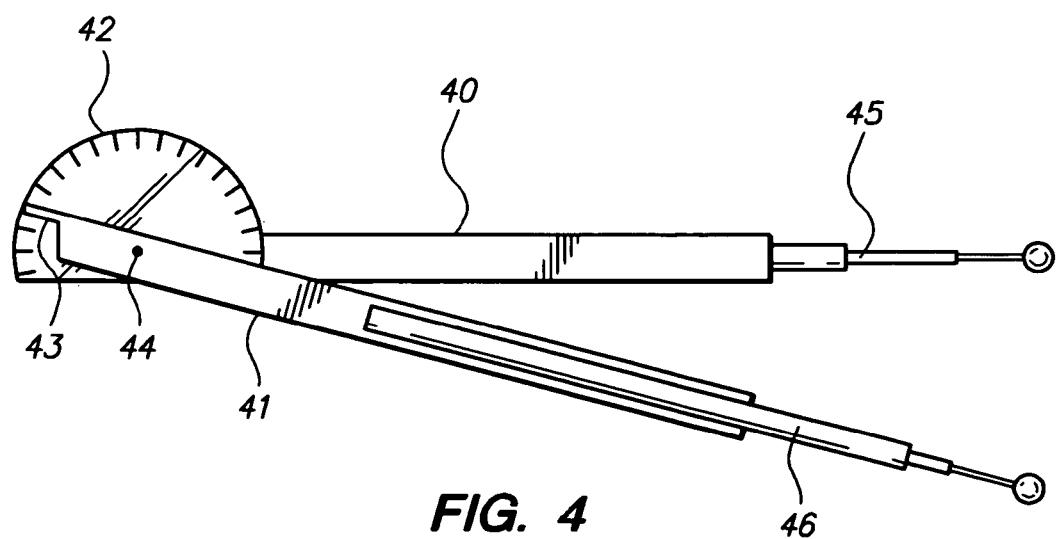
FIG. 4. is a plan view of the invention made of metal.

In another preferred embodiment, illustrated in FIG. 4, the two arms and the fastener are made of metal or other heat resistant material to allow high-pressure steam sterilization for use of this device during a surgical operation. FIG. 4 shows a Plan View of the device comprising arm 40 with degree markings 42, arm 41 with indicator mark 43, and fastener 44 creating a pivot point at one end. The new features of the present invention are methods or means on one or both arms for extending the length of said arm or arms with the ability of said method or means to retract or shorten said arm or arms to the original size. In the particular device illustrated the means for extending and contracting the length of one or both arms is accomplished by affixing telescoping sleeves aligned along the central axis of the arm or arms. In FIG. 1 telescoping sleeves 15 are affixed to arm 10, and telescoping sleeves 16 are affixed to arm 11. FIG. 2 shows telescoping sleeves 23 affixed to arm 21 and telescoping sleeves 24 affixed to arm 20. Similarly, in FIG. 3 telescoping sleeves 33 are affixed to arm 31 at the end opposite to fastener 32, and telescoping sleeves 34 are affixed to arm 30 at the end opposite to fastener 32. In FIG. 4 telescoping sleeves 45 are affixed along the central axis of arm 40, and telescoping sleeves 46 are affixed along the central axis of arm 41.

In the preferred and illustrated embodiments the telescoping sleeves shown in FIGS. 1-4 are comprised of tubular and solid metal (or other heat resistant material) allowing the invention to be carried easily in a clothing pocket to be readily available for measuring various anatomic angles with accuracy. In use the pivot point is placed at the apex of the angle to be measured, one or both arms are extended to the anatomic landmark or landmarks desired, and the angle between these two landmarks will be indicated and measured on the angular markings provided on one of the arms. Once the measurement is completed, the sleeves can be easily retracted to their original state for ease of portability.

The method for extending and retracting the length of one or both arms may be done in various ways without departing from my invention, said method or methods might consist of sliding elements or folding elements incorporated into the arm or arms of the device.

The material used to construct the device can be selected without departing from my invention; said material could be thicker, larger, and heavier in order to improve durability but decreased ease of portability.

A circle of larger diameter for the degree markings could be used without departing from my invention; said circle of larger diameter might improve accuracy of measurement but would increase the size and decrease the ease of portability of the device.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. A device for measuring anatomic angles, said device comprising:
   a pair of identical elongated arms each characterized by a flat top surface, a flat bottom surface, a pair of parallel opposing side surfaces, a semi-circular pivot end surface and an opposing free end surface, the semi-circular pivot end surface having a diameter equal to the distance between the pair of parallel opposing side surfaces;
   the elongated arms being pivotally connected to one another at a pivot point which is located at the origins of the semi-circular pivot end surfaces, with the flat top surface of one of the elongated arms slidably engaging the flat bottom surface of the other of the elongated arms;
   one of the elongated arms having degree markings formed thereon around the pivot point and the other of the elongated arms having a marker formed thereon to indicate an angle between the two elongated arms; and a pair of identical telescoping sleeves, one of the telescoping sleeves being mounted to the top surface of one of the elongated arms in alignment with the pivot point and telescoping relative to the free end surface of that elongated arm, and the other of the telescoping sleeves being mounted to the bottom surface of the other of the elongated arms in alignment with the pivot point and telescoping relative to the free end surface of that elongated arm;

said device being sufficiently small and lightweight to allow ease of portability in a clothing pocket.

2. A device according to claim 1 wherein said elongated arms are made of lightweight, clear plastic.

3. A device according to claim 1 wherein said elongated arms are made of heat resistant material.

4. A device according to claim 1 wherein said telescoping sleeves are made from at least one of the group consisting of metal and other material.

5. A device according to claim 1 wherein said telescoping sleeves comprise at least three sliding elements.

6. A device according to claim 1 wherein one of said telescoping sleeves is in an expanded condition and one of said telescoping sleeves is in a retracted condition.

7. A device according to claim 1 wherein said telescoping sleeves extend beyond the opposing free end surfaces of the elongated arms when said telescoping sleeves are in a retracted condition.

8. A device according to claim 1 wherein said telescoping sleeves have a diameter which is greater than the thickness of said elongated arms.

9. A device for measuring anatomic angles, said device comprising:

a pair of identical elongated arms each characterized by a flat top surface, a flat bottom surface, a pair of parallel opposing side surfaces, a semi-circular pivot end surface and an opposing free end surface, the semi-circular pivot end surface having a diameter equal to the distance between the pair of parallel opposing side surfaces;

the elongated arms being pivotally connected to one another at a pivot point which is located at the origins of the semi-circular pivot end surfaces, with the flat top surface of one of the elongated arms slidably engaging the flat bottom surface of the other of the elongated arms;

one of the elongated arms having degree markings formed thereon around the pivot point and the other of the elongated arms having a marker formed thereon to indicate an angle between the two elongated arms; and a pair of identical folding elements, one of the folding elements being mounted to the top surface of one of the elongated arms in alignment with the pivot point and unfolding relative to the free end surface of that elongated arm, and the other of the folding elements being mounted to the bottom surface of the other of the elongated arms in alignment with the pivot point and unfolding relative to the free end surface of that elongated arm;

said device being sufficiently small and lightweight to allow ease of portability in a clothing pocket.

10. A device for measuring anatomic angles, said device comprising:

a pair of identical elongated arms each characterized by a flat top surface, a flat bottom surface, a pair of parallel opposing side surfaces, a semi-circular pivot end surface and an opposing free end surface, the semi-circular pivot end surface having a diameter equal to the distance between the pair of parallel opposing side surfaces;

the elongated arms being pivotally connected to one another at a pivot point which is located at the origins of the semi-circular pivot end surfaces, with the flat top surface of one of the elongated arms slidably engaging the flat bottom surface of the other of the elongated arms;

one of the elongated arms having degree markings formed thereon around the pivot point and the other of the elongated arms having a marker formed thereon to indicate an angle between the two elongated arms; and a telescoping sleeve being mounted to one of (i) the top surface of one of the elongated arms in alignment with the pivot point and telescoping relative to the free end surface of that elongated arm, and (ii) the bottom surface of the other of the elongated arms in alignment with the pivot point and telescoping relative to the free end surface of that elongated arm;

said device being sufficiently small and lightweight to allow ease of portability in a clothing pocket.

\* \* \* \* \*